United States Patent
Delia (10) Patent No.: US 10,321,879 B2
(45) Date of Patent: Jun. 18, 2019

(54) MULTIPLE SENSOR WIRELESS WEARABLE PULSE OXIMETER-BASED DEVICE

(71) Applicant: Diego Alejandro Delia, Ciudad de Buenos Aires (AR)

(72) Inventor: Diego Alejandro Delia, Ciudad de Buenos Aires (AR)

(*) Notice: Subject to any disclaimer, the term of this patent is extended or adjusted under 35 U.S.C. 154(b) by 161 days.

(21) Appl. No.: 15/134,553

(22) Filed: Apr. 21, 2016

(65) Prior Publication Data

US 2016/0310085 A1    Oct. 27, 2016

Related U.S. Application Data

(60) Provisional application No. 62/151,152, filed on Apr. 22, 2015.

(51) Int. Cl.

| | |
|---|---|
| *A61B 5/00* | (2006.01) |
| *A61B 5/024* | (2006.01) |
| *A61B 5/1455* | (2006.01) |
| *A61B 5/11* | (2006.01) |
| *A61B 5/18* | (2006.01) |

(52) U.S. Cl.
CPC .......... *A61B 5/746* (2013.01); *A61B 5/02405* (2013.01); *A61B 5/02438* (2013.01); *A61B 5/14551* (2013.01); *A61B 5/6804* (2013.01); *A61B 5/6806* (2013.01); *A61B 5/742* (2013.01); *A61B 5/7455* (2013.01); *A61B 5/1112* (2013.01); *A61B 5/18* (2013.01); *A61B 5/4818* (2013.01); *A61B 5/7203* (2013.01); *A61B 5/7445* (2013.01)

(58) Field of Classification Search
CPC ............ A61B 5/02405; A61B 5/02438; A61B 5/1112; A61B 5/14551; A61B 5/18; A61B 5/4818; A61B 5/6804; A61B 5/7203; A61B 5/742; A61B 5/7445; A61B 5/7455; A61B 5/746
USPC .................................................. 600/300, 301
See application file for complete search history.

(56) References Cited

U.S. PATENT DOCUMENTS

| | | | |
|---|---|---|---|
| 6,510,331 B1 | 1/2003 | Williams et al. | |
| 8,430,817 B1* | 4/2013 | Al-Ali ................. | A61B 5/7221 600/301 |
| 8,554,297 B2 | 10/2013 | Moon et al. | |
| 8,620,448 B1 | 12/2013 | Delia | |
| 9,320,441 B1* | 4/2016 | Hays ........................ | A61B 5/02 |
| 2006/0079794 A1* | 4/2006 | Liu .................... | A61B 5/14552 600/502 |
| 2007/0167844 A1* | 7/2007 | Asada .................... | A61B 5/022 600/485 |
| 2009/0326354 A1* | 12/2009 | Mao ................... | A61B 5/14532 600/344 |
| 2012/0046532 A1* | 2/2012 | Chang ................ | A61B 5/02438 600/324 |

(Continued)

*Primary Examiner* — Michael J Carey
(74) *Attorney, Agent, or Firm* — Crowell & Moring LLP (57) ABSTRACT

A multiple sensor wireless wearable device measuring oxygen saturation and/or heart rate includes a single housing, two or more sensors, each having a pick up beam, an alarm generator, and a timer generator. The two or more sensors, the alarm generator, and the timer generator are all housed inside the single housing, and the two or more sensors are placed in specifically selected placements that avoid their respective pick up beams crossing each other. The housing is a garment specifically designed for containing the device.

22 Claims, 6 Drawing Sheets

(56) References Cited

U.S. PATENT DOCUMENTS

2014/0200423 A1    7/2014  Eisen et al.
2014/0358012 A1*  12/2014  Richards ............ A61B 5/02438
                                                    600/479
2016/0135706 A1*   5/2016  Sullivan ............... A61B 5/0059
                                                    600/301

* cited by examiner

MULTIPLE SENSOR WIRELESS WEARABLE PULSE OXIMETER-BASED DEVICE

This application claims priority under 35 U.S.C. 119(e) to U.S. provisional application Ser. No. 62/151,152, filed Apr. 22, 2015, the entire disclosure of which is incorporated herein by reference.

BACKGROUND OF THE INVENTION

1. Field of the Invention

The present invention refers to a wireless wearable pulse oximeter-based device that is based on signals supplied by two or more sensors, contained in a single housing to reduce false alarms.

A wireless wearable device measures blood oxygen saturation and/or heart rate based on two or more sensors placed in different positions of the user's body, wherein the two or more sensors share a single housing and in which the sensors are preferably of the same type. When all the sensors detect a measured value below a set of predetermined threshold values, an alarm is immediately triggered. There are different situations of the detections of the sensors that may cause the alarm to be triggered depending on a safety algorithm. The alarm can be audible, a tactile stimulus or a wireless transmitted signal sent to a receiver as, for example, a central monitoring system or a Smartphone. The wearable device can be adapted to be housed inside a wrist watch or an intelligent wrist band or on a glove. The information obtained by the sensors may be received by the device or alternatively be sent to another one.

2. General Description of the Related Art

The Obstructive Sleep Apnea Syndrome (OSAS) is a very common pathology; nearly 18 million people suffer nowadays this sickness in the USA. Several treatment approaches are available, for example the use of CPAP (Continuous Positive Airway Pressure) masks or mouth devices. The object of the present invention is to help the patients to reduce hypoxia episodes while sleeping to avoid worsening their clinic situation.

On the other hand, the Sudden Infant Death Syndrome (SIDS) might typically occur in infants one month through one year of age. It can happen to healthy children who, suddenly and inexplicably, never wake up and die. In the USA, statistics indicate that 6-7 infants die every day due to this unfortunate event and, although there are several theories that try to explain it cause, there still exists no certainty for knowing its origin.

The pulse oximeter is a well-known device that uses technology that is available since the eighties. It is non-invasive and is suitable for taking measurements on the finger of the hand. It may be obtained in several versions, for example included in multiparametric monitors connected to a central station or otherwise in portable devices. Nowadays, several technology companies are developing technical solutions for embedding them inside wrist watches of Smartphones The following prior art documents were located:

Document U.S. Pat. No. 6,510,331 B1 (Switching device for multi-sensor array) describes a switching device interposed between a conventional oximeter and a plurality of conventional photosensors. The photosensors are located on different limbs of the body. The switching device may be operated in the manual mode or an automatic mode. In the manual mode each different photosensor may be individually selected to provide the input signal to the oximeter. In the automatic mode, the switching device scans the incoming signals from the different photosensors and forwards the best, strongest or least distorted signal to the oximeter. The device prevents the loss of oximetry information due to interrupted blood flow in a particular part of the body or the failure of a sensor. However, the device of the present invention is not located on different limbs of the body and, therefore, allows a much comfortable usage for the user.

The specification of the cited patent describes in column 2, line 12: "A switching device interposed between an oximeter and a plurality of photosensors located on various body extremities." In column 2, line 30 the specification describes: "It is another object of this invention to provide a switching device interposed between the array of sensors and the analyzer section for selection of a particular incoming signal from one of the sensors." However, the device of the present invention does not interpose any switching device between the sensors and the processor and, unlike the present invention, the arrangement of the US patent is not housed in a single housing.

Also, in column 2, line 41 the specification of the cited patent reads: "The switching device of this invention need not be restricted to pulsoximetry but can be used in other general measuring systems in which plural sensors are arrayed with a single display mechanism." This suggests that the switching device can be used for measuring other type of signals, which means it is not specifically designed for being used in pulsoximetry. However, the device of the present invention is specifically designed for measuring oxygen blood saturation (Sat $O_2$), heart rate and/or Heart Rate Variability (HRV) and in this device the user is able to deactivate any of these measurement functions. In a preferred embodiment in which the user uses the device of the present invention to avoid falling asleep (e.g. a long distance truck driver) he may deactivate the Sat $O_2$ function.

In column 2, line 59 the specification of the cited document reads: "The switching device 10 is shown operatively connected to an oximeter/analyzer section 11 by output cable 13, in FIG. 1." However, the device of the present invention does not include user accessible sensor connection cables and all the signal connections are embedded in the overall housing (e.g. the glove). The text of the cited document reads further: "The oximeter/analyzer section 11 and display 12 are well known in the art and operate to alternately energize the sensors 30 (shown in FIG. 3). This may let the reader infer that the oximeter/analyzer is energized by an external power supply. However, in the present invention the electrical power is supplied by a rechargeable battery.

In column 2, line 66, the specification of the cited document reads: "The switching device 10 is illustrated in the general form of a rectangular housing 14," This allows the reader to infer that the sensors are not housed in housing 14 of the switching device 10 and are connected to it by means of cables. However, in the present invention all the elements (circuitry and sensors) are housed in a single housing (e.g. a glove).

In column 3, line 11, the specification of the cited document reads: "As shown in FIG. 1, the input connections 20 each go to an individual sensor located on a part of the body as labeled on the face of the box 14." Here again the text mentions sensor cabling.

The cited document further reads "The sensor signals are scanned and the first or most acceptable signal is forwarded to the analyzer section. If a signal is lost, the switching device immediately selects another sensor." The switching device analyzes the signals and selects another sensor. However, the present invention does not select or discriminate among the various sensors since all of them operate at the same time and, if all of them measure a value below a predefined threshold, the alarm generator triggers the alarm.

The cited document further reads: "The connection 20 carries power and the return signal." However, in the present invention there is no wired power supply connection because it is housed inside the same housing.

The cited document further reads: "As shown in FIG. 3, line 24 and line 20 are connected through a plug-in on the casing 25." However, the device of the present invention requires no external power supply.

The cited document further reads: "It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings." It is apparent that the document fails to reveal a wearable or wireless device and, therefore, it is totally inadequate for home usage.

U.S. Pat. No. 8,554,297 describes a body-worn system that continuously measures pulse oximetry and blood pressure, along with motion, posture, and activity level, from an ambulatory patient. The system features an oximetry probe that comfortably clips to the base of the patient's thumb, thereby freeing up their fingers for conventional activities in a hospital, such as reading and eating. The probe secures to the thumb and measures time-dependent signals corresponding to LEDs operating near 660 and 905 nm. Analog versions of these signals pass through a low-profile cable to a wrist-worn transceiver that encloses a processing unit. Also within the wrist-worn transceiver is an accelerometer, a wireless system that sends information through a network to a remote receiver, e.g. a computer located in a central nursing station. The present invention uses no cables whatsoever and also uses several sensors.

Document US 2014/200423 A1 (Wearable pulse oximetry device) describes a pulse oximetry device that is mounted on a wrist strap and fixates an area above a distal end of the ulna with a dome shaped structure. This area is used as measuring area. The measurement is carried out by a detector positioned above the fixated area that detects light emitted by light sources having different wave lengths that are located at a periphery of the fixated area. Hence, the reflections are measured at neither a reflection mode nor a transmission mode, but are at an angle between 20 DEG and 160 DEG from the emitted light. This mode, termed trans-illumination, allows achieving an excellent signal to noise ratio that for the first time enables continuous and reliable measurement of oximetry data on the wrist. The present invention uses several equal sensors. Also, the present invention can provide electric stimuli in the event an alarm is triggered.

U.S. Pat. No. 8,620,448 A1 (Non-invasive, wireless, portable device applicable to the finger to reduce the risk of sudden infant death syndrome and reduce the risk of apnea, slower heart rate, and heart arrest in all age groups) describes a device of the same applicant. However, the present invention uses several sensors inside a single housing and its object is to add more novel features to what is already described in U.S. Pat. No. 8,620,448.

Other new techniques are showing up every day, such as the single-sensor devices developed by MASIMO® (http://masimo.com/aboutmasimo/index.htm) which seem to better pick up signals even under movement and show enhanced sensitivity.

SUMMARY OF THE INVENTION

One of the most important issues to be solved in the oximeter based devices is that they might trigger false alarms, thus creating confusion to caregivers that are in charge of monitoring patients or themselves. These false alarms are most commonly triggered due to the user's body movement, or a movement of his hand, or because the device is placed on a poor blood irrigated body zone or because an intense ambient light masks the infrared sensor beam. The object of the present invention is to minimize the issuance of these false alarms.

The inventor has found out that one of the best ways to minimize false alarming in this type of devices is to measure in a first preferred embodiment the patient's parameters with two or more sensors.

In another preferred embodiment the signals of the at least two sensors is submitted to a very specific algorithm that checks the validity of the numeric data measured by each of the sensors before triggering an alarm.

The main advantage in using multiple sensors in the device is that false alarms are greatly reduced. In some favorable situations in which the patient is next to the caregiver, if the device measures abnormal values that do not seem to match the patient's apparent health situation, or if the device does not measure numeric values at all, the caregiver is still capable of changing the placement of the device from one finger to another one. Also, if the patient is under a surgical procedure, the intervening professional may use two oximeter devices on separate fingers to make sure that at least one safe signal is received. However, this particularly favorable scenario is by far the least usual one and chances are that the patient is quite far away from his caregiver. Most frequent signal failure may be due to device misplacement, poor blood irrigation or to intense ambient light.

Evidently, none of the designers of the known oximeter-based devices were able to acknowledge the benefits of using more than one sensor simply because it was necessary to develop a smaller and simpler device that may avoid higher costs and complexity when doing so.

In a first preferred embodiment, one of the at least two sensors measures blood oxygen saturation and another one of the at least two sensors measures heart rate.

In another preferred embodiment, the device according to claim 1, wherein one of the at least two sensors measures Heart Rate Variability (HRV)

In a further preferred embodiment, one of the at least two sensors and the other one of the at least two sensors measure the same parameter.

Figure 2:
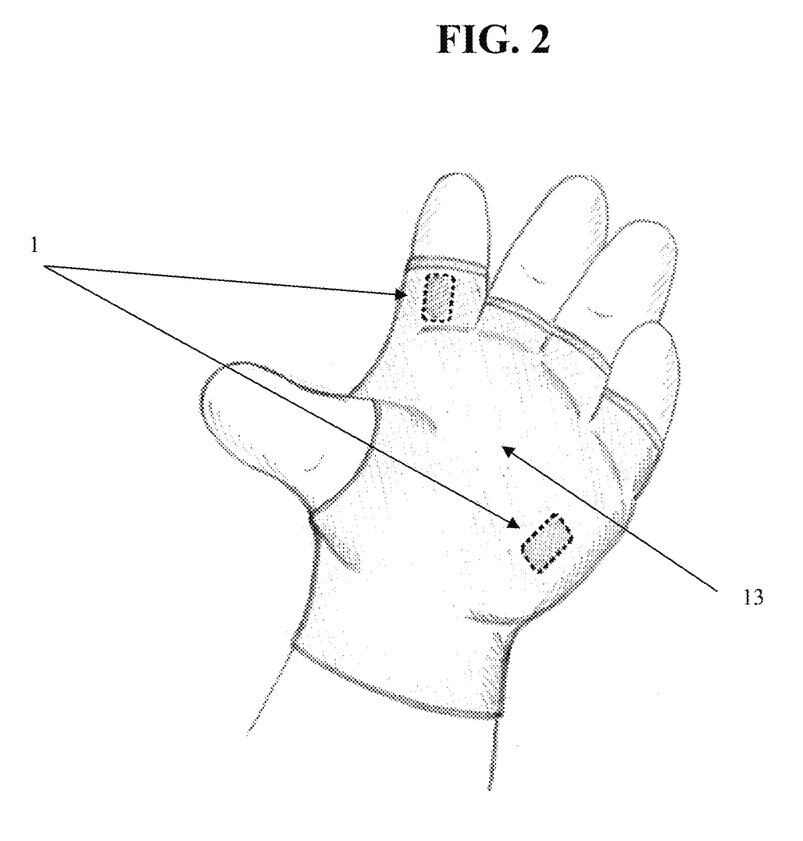
FIG. 2 schematically shows a preferred embodiment of the device of the present invention placed on the hand of a baby and comprising two sensors.

Particularly, the sensor placement design of a multi-sensor oximeter-based device must take in account that the multiple reception sensor beams should never cross each another if these are simultaneously active. A first approach to solve this issue is to place a single sensor in each finger, particularly in adults due to the bigger hand size. However, when used in children, it is recommendable not more than two sensors to be used due to their smaller hand or foot size and the sensors would be placed on most separated placements of the housing (FIG. 2).

The main target of device of the present invention is to solve the false alarming since the caregivers and/or the users usually are unable to distinguish whether the measured values are normal or not, and also unable to solve sensor signal failure. When using the device of the present invention, the caregiver has no need to change the sensor placement from one finger to another and, therefore, the performance of the device is greatly enhanced.

In the design of the device of the present invention the use of a complementary specially designed algorithm is essential for evaluating the measured signal quality. With the main use of several sensors, thanks to the algorithm the microprocessor is capable of deciding whether an alarm is originated by a signal average value that is above its safety threshold or if it is originated by an individual faulty sensor, such as may be seen in FIG. 4. The use of the algorithm is essential for letting the device decide to trigger the alarm at the right moment.

It is important to point out that, in the algorithm logic, the timer 1 (T1) might be bypassed if the inventor finds out in future developments that the alarm can be triggered right away even if a single sensor is picking up abnormal values and the other sensors do not pick up numeric values at all. In this embodiment, only timer 2 (T2) would be used and might be renamed as being timer T.

On the other hand, if the microprocessor is programmed to trigger an alarm based on average sensor signals, the algorithm is simplified and does not follow the logic shown in FIG. 4 and the alarm is simply triggered whenever the average value is below a predetermined threshold value. This average value is calculated from the sensors that pick up valid numeric values.

If the designed logic only uses the heart rate signal and/or the heart rate variability and the oxygen saturation signal is deactivated a useful feature to add to the device is the GPS function. In this embodiment, the microprocessor automatically decides, without the user's intervention, the alarm threshold triggered by a constant user's speed exceeding this value during a predetermined time period. In this alternative embodiment, the algorithm shown in FIG. 4 only takes in account the numeric values of the image. In other words, if no numeric value is picked up, no alarm will ever be triggered. Therefore, to take in account the risk for the user of falling asleep, both timers T1 and T2 are bypassed to allow the device's reaction to be immediate.

The technical solution achieved by the present invention cannot be considered obvious by the skilled in the art because it was designed and developed by the inventor who is faced every day with oximeter sensor issues mainly originated by pick up misplacement or sensor wreckage. The invention solves the requirement of having to continuously reposition, choose or replace oximeter sensors applied to the patients' fingers in healthcare rooms.

The device of the wearable present invention comprises a microprocessor in charge of processing the information received from several sources, for example, the multiple pulse oximeter sensors. The microprocessor may be contained inside a housing comprising, for example, a glove or any other wearable clothing. This glove or wearable clothing comprises two electrodes which are used to apply a transcutaneous electrical nervous stimulation, and the alarm may be chosen to be either an electric stimulus or a mechanical vibration on the user, as long as the selected alarm was electric stimulus deliverance. In a preferred embodiment, the glove or wearable clothing comprises a speaker to make noise when the alarm to be used is the audible alarm.

The sensor of the present device shows the measured values in an independent way on the device's display or, alternatively on the display of a remote device. In other alternative embodiments, the microprocessor stores averages of the values measured by all the sensors, or only by those sensors that measure valid numeric values. In the alternative embodiment, the alarm triggering is safer because it is based on a single value, namely the measured average value.

The pulse oximeter measures blood oxygen saturation and heart rate. Several methods for pulse and oximetry measurements are available. In one of them, the device emits two wavelengths of light by means of two LEDs to a photodetector through a translucent part of the user's body, usually a finger or an earlobe. It measures the changing absorbance at each of the wavelengths allowing it to determine the absorbances due to the pulsing arterial blood. One of the LEDs emits 660 nm wavelength red light and the other one emits infrared light, with a wavelength in the range of 905, 910 or 940 nm. The absorbance to these frequencies in the oxyhemoglobin is greatly different to the one in the desoxihemoglobin; therefore a difference between the oxyhemoglobin and the desoxihemoglobin may be calculated from the relation of red and infrared absorbance. Nowadays, other oximetry pulse detection methods are known, such as detection by reflectance and other even more sophisticated ones.

The heart rate variability (HRV) can also be measured which is more useful for those users attempting to avoid falling asleep (the HRV disturbance is related to the moments prior to this event, especially if the alarm signaling is tactile or via electrical stimuli). However, the normal limits are not clearly defined. An HRV disturbance might be related to several different pathologies such as myocardium infarct, congestive cardiac insufficiency, diabetic neuropathology, SIDS susceptibility, and so on. The main object of the present invention is to use more than a single beam, that is, at least two sensors in a single housing to minimize the issuance of false alarming (see FIGS. 1 and 2).

DETAILED DESCRIPTION OF THE INVENTION

The concept developed by the inventor to implement the use of more than one sensor in the device was not straightforward and required careful design considerations. These will be fully explained in the following paragraphs.

Figure 1:
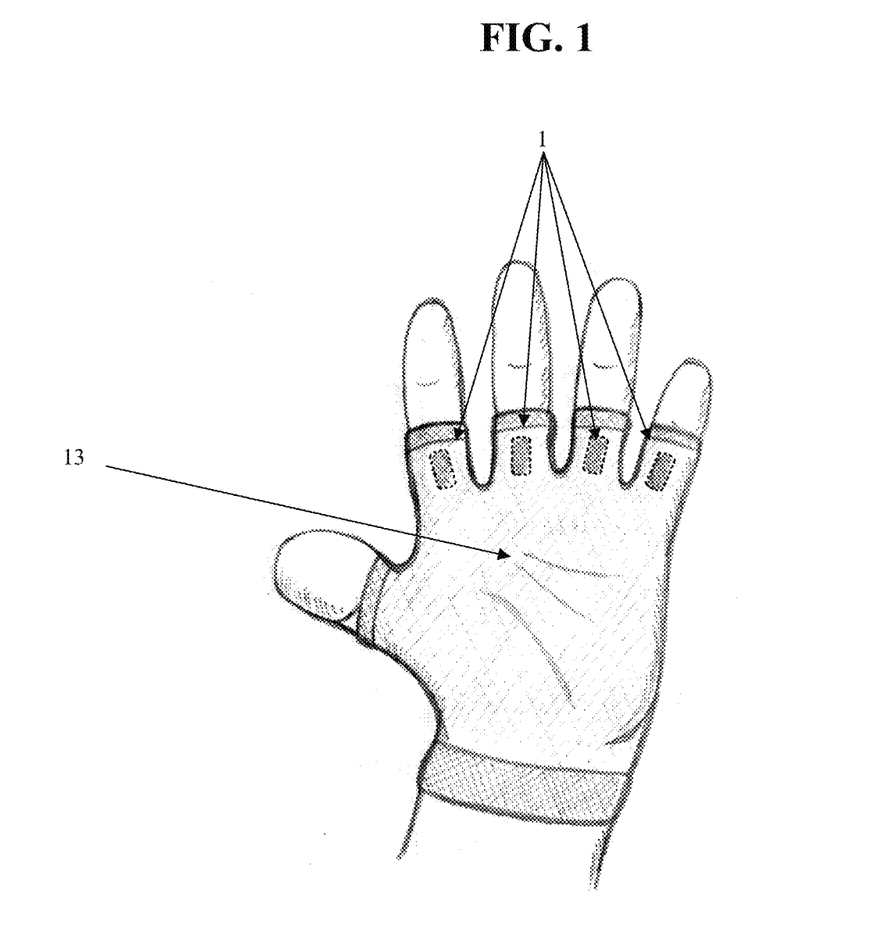
FIG. 1 schematically shows a preferred embodiment of the device of the present invention in the form of a glove comprising five sensors, placed on the finger bases.

FIG. 1 shows an adult hand garment 13, for example a glove, containing the device's hardware housed inside the casing 12 (not shown) and the sensors 1, placed at their precise locations, The elements shown in dotted lines are not visible to the user and are placed inside the garment. FIG. 1 shows that a preferred placement the placement of each of the sensors is on the base portion of each finger.

FIG. 2 shows a baby hand garment 13, for example a glove, containing the device's hardware housed inside the casing 12 (not shown) and the sensors 1, placed at their precise locations, The elements shown in dotted lines are not visible to the user and are placed inside the garment. FIG. 2 clearly shows that, due to the small size of a typical baby's hand, one of the sensors should be placed on one finger, preferably on the index finger, and the other sensor may be placed on a zone of the palm hand at a portion near the base of the hand and distal from the thumb or even on the wrist.

Figure 3:
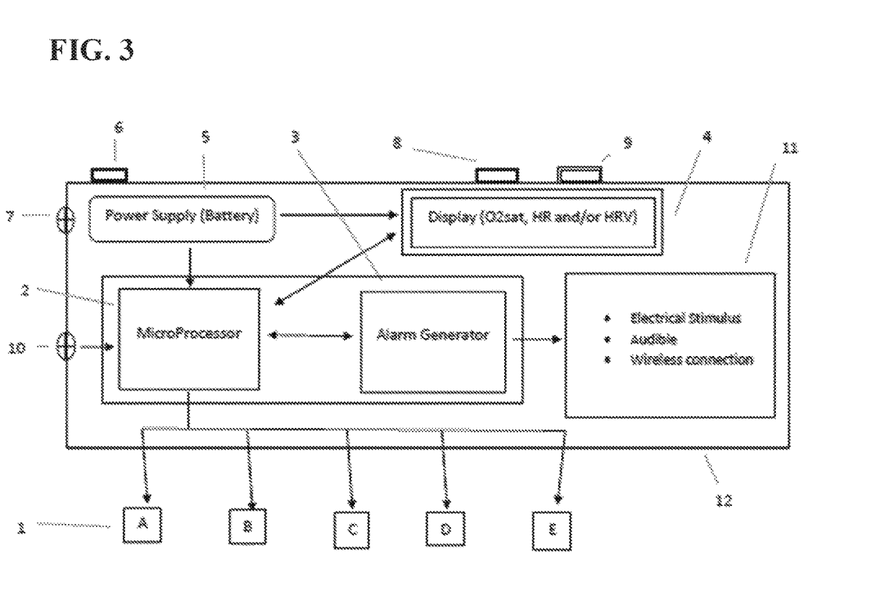
FIG. 3 shows a block diagram of an embodiment of the device of the present invention connected to five sensors. If the alarm is triggered by means of electrical stimulation, two electrodes will be mounted outside the casing.

FIG. 3 shows a preferred embodiment having five sensors 1 placed outside of the device casing 12 containing the microprocessor 2 that controls the sensor signals A-E. When the microprocessor detects that all the sensor signals A-E are below a predetermined threshold value, or when there are no sensor signals within a predetermined normal range, the microprocessor outputs a signal to the alarm generator block 11. All the useful information is shown to the user via a display 4 and the circuitry is powered by means of the power supply 5 which is activated by means of the ON/OFF switch 6. The threshold values are set by means of the press buttons 8 and 9. At the left of the casing 12, a jack connector 7 is foreseen for connecting a cable for recharging the power supply consisting of rechargeable batteries, using an external power charger. Also a USB connector 10 allows connecting a Smartphone and/or a notebook for reprogramming the microprocessor. In another preferred embodiment, the connection may be WI FI, Bluetooth, or other wireless connection. The battery should last for up to approximately 10 hours and the device may communicate via a wireless communication to a central monitor or a Smartphone in order to store the collected measurement signals for further analyzing the results.

In the preferred embodiment of FIG. 3, the sensors A-E are placed outside of the casing 12 but inside the single overall housing formed by the device glove, in positions near to each other but without interfering in their signal reception. Once the user turns the device on, all the sensors are activated and send their measurement signal to the circuitry to be shown in the display 4 of the casing 12.

In any of the home version garment embodiments, the garment material is washable and, for doing so without any risk of damaging the electronics, the casing can be extracted from the garment In the embodiments to be used in healthcare premises, the device might be dispensable, which implies using ordinary non-washable materials and hence allowing a much simpler design. In this version, the device could be energized from an external power supply, thus preserving the life of the internal battery.

In the wrist band or wrist watch embodiments the hardware cannot be extracted because the whole device is contained inside the band. The sensors are mounted around the inner part of the band that contacts the wrist. In other embodiment, the device can be placed on the ankle.

In the various embodiments of the garment several fixing systems may be used. These may be elastic and/or hold by VELCRO® based fasteners or similar ones. The several fastener systems may be particularly useful if the user is a baby.

The sensors may be placed on one or more fingers or on different zones of the palm hand and these placements will depend on the actual size of the user's hand. The preferred embodiment of the invention may also be used on a foot, particularly if the user is a baby.

The user may carry out changes in the alarm limits by means of the buttons 8 and 9 adapted for this use and has also the possibility of selecting a function in the alarm generator block (FIG. 3). If the sensors are not receiving any signal the user can choose to generate no alarm at all or else he can set the device so that the processor triggers a timer with an approximate delay of 10 seconds. In another scenario, if the sensors are all receiving signals below a certain predetermined alarm triggering threshold value the generator will trigger the alarm output signal without delay. A further scenario can be that one of the sensors measures a value below the predefined alarm threshold and another sensor receives no signal, in which case the user may decide to program the device to immediately trigger the output alarm signal or else to trigger the timer to create a delay in this output signal (FIG. 4). It is important to point out that this algorithm was designed for processing both parameters: SpO2 and HR. As soon as the alarm is triggered by one of the parameters, the timer of the other parameter is deactivated.

Figure 6:
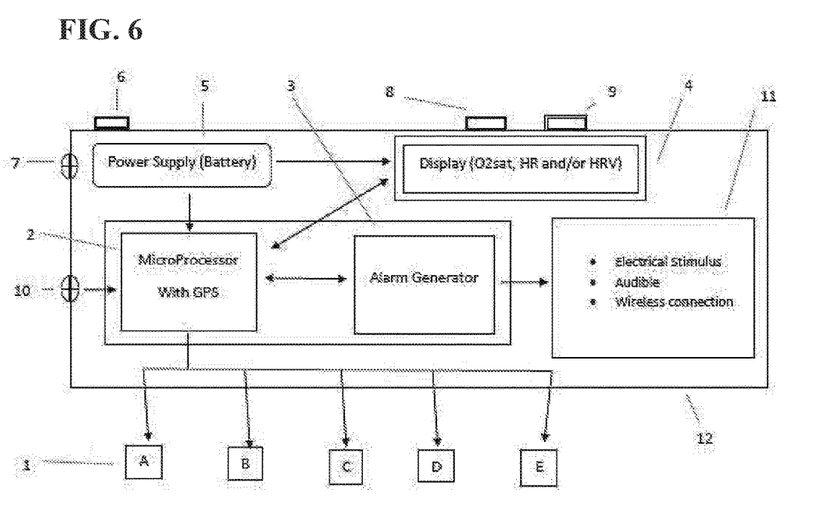
FIG. 6 shows a block diagram of an embodiment of the device of the present invention connected to five sensors. In this embodiment, we can see the GPS included in the microprocessor. If the alarm is triggered by means of electrical stimulation, two electrodes will be mounted outside the casing.

Other device's features are that, whenever it is used to keep a vehicle driver from falling asleep, it may contain a GPS handled by the microprocessor (FIG. 6). As soon as the device detects constant vehicle speed greater than a predetermined value (e.g. 90 km/h) during a predetermined period (e.g. 10 minutes) a personalized and autonomous alarm threshold setting program is activated for the user. The device can estimate an average heart rate value and the microprocessor will define a threshold for triggering the alarm. This threshold may be in a range of 5 to 10% below the previously estimated average value. This feature is essential since it allows the device establish adequate setting without the need of the intervention of the user and allows the device to better trace the optimum settings which will eventually arrive to the optimum moment for triggering the alarm.

Also, the GPS allows a third person to locate the geographical place where user is located. In some duties, such as for example security guards, the alarm limits will be independent of GPS. The alarm limit will be set by the user, or alternatively the microprocessor will set it by means of an algorithm, selecting the most reliable limit for that particular person.

In another scenario, in order to avoid false alarming the device is programmed to keep on hold the alarm triggering if one of the sensors is measuring normal values, even though the rest of the sensors are measuring abnormal ones.

All the device programming may be done pressing buttons 8 and 9 and watching the result on the display or in an alternative embodiment it may be done from another device 11 such as a Smartphone or a computer, via a USB connection 10. In another preferred embodiment, the connection may be WI FI, Bluetooth or other wireless connection.

The device of the present invention foresees that each parameter measurement can be linked to any of these alarming alternatives in an individually independent way. In other words, as soon as one of the parameters (SpO2 or HR or HRV) measures a value falling below the predetermined threshold, the alarm generator is activated to carry out the programmed action.

The device of the present invention has multiple functions. In a preferred embodiment the device generates an alarm signal together with a transcutaneous electrical nervous stimulation, sufficient to make the user react when being under certain abnormal physical conditions. In one embodiment the device may be used to generate the reaction of a user being asleep and suffering a condition of sleeping obstructive apnea. In this case, a mild electrical stimulation should produce an immediate liberation of the breathing path. The device can also be adapted to any other device based on pulse oximetry and needing the reduction of false alarming. The user is able to deactivate any parameter if required, especially if the function is related to detecting weariness due to somnolence, that is, turning off the detection of SpO2.

When the alarm to be used consists of a transcutaneous electrical stimulation, the device will include two electrodes placed near the sensors, and are in charge of applying the electric discharge on the user to make him react. The device is designed to keep the electric stimuli within safe values.

The present invention can also be applied to the device designed to avoid many different situations where hypoxia and/or bradycardia are critical, described and claimed in U.S. Pat. No. 8,620,448 of the same inventor as the present document. It is vital in this type of devices and any other similar ones sold all over the world to minimize any possible false alarms.

Figure 4:
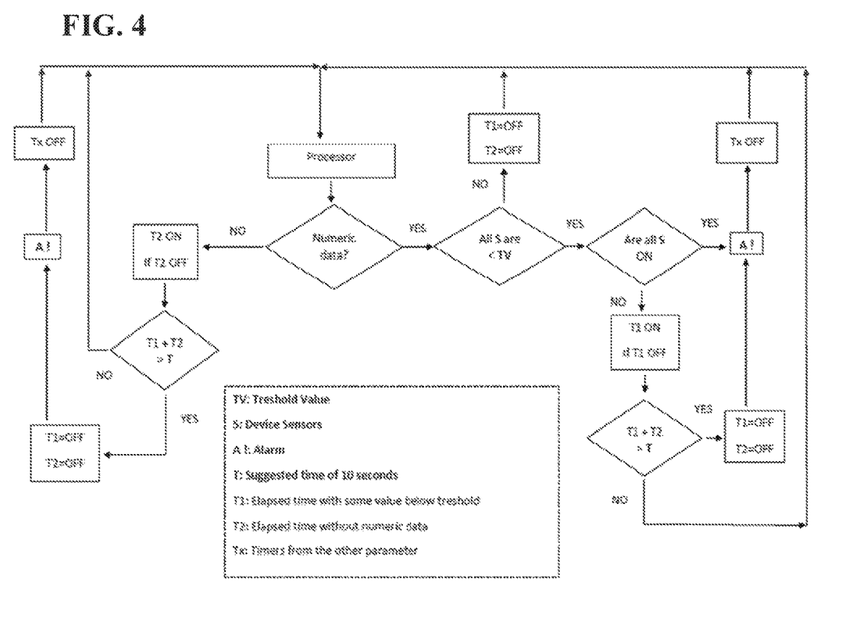
FIG. 4 shows a flow chart of an algorithm specially designed for the device of the present invention.

FIG. 4 shows an algorithm which was specially designed for being used in the multiple sensor device and foresees several scenarios. When all the sensor signals are below a predefined value, the alarm generator triggers the alarm. Also, when any of the sensors measures a signal below a predefined value and the other sensors receive no signal at all, in one embodiment the alarm generator triggers a timer and in other embodiment it triggers the alarm. If none of the sensors receives a signal a timer is triggered. Also, if any of the sensors measures a normal value, all the timers are deactivated.

Figure 5:
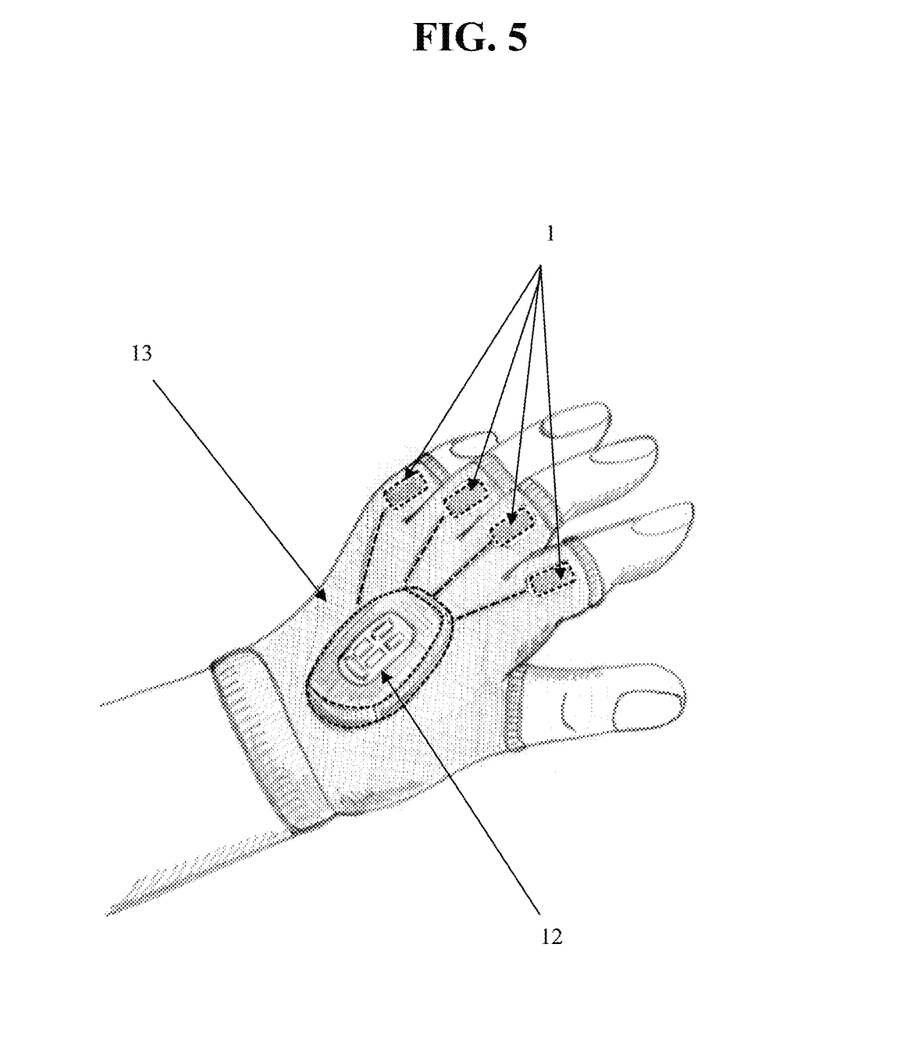
FIG. 5 shows a schematic view of the full device applied to a Smart wrist band also containing the power supply. The figure shows a free end portion of the hand but in other preferred embodiments, the invention might be formed only by a wrist band or a wrist watch.

FIG. 5 shows an alternative embodiment of an adult hand garment 13, for example a glove, containing the device's hardware housed inside the casing 12 and the sensors 1, placed at an alternative placement, The elements shown in dotted lines are not visible to the user and are placed inside the garment.

FIG. 6 shows a block diagram of an embodiment of the device of the present invention connected to five sensors 1. In this embodiment, it may be seen the GPS included in the microprocessor. If the alarm is triggered by means of electrical stimulation, two electrodes will be mounted outside the casing (not shown).

I claim:

1. A multiple sensor wireless wearable device measuring parameters comprising oxygen saturation and/or heart rate, said device usable on a hand of a user and comprising:
a single housing comprising a hand garment,
two or more pulse oximeter sensors each having a pick up beam,
an alarm generator for delivering an alarm related to the measurement of said parameters, and
a timer generator,
wherein said two or more sensors, said alarm generator and said timer generator are all housed inside said hand garment,
wherein said two or more sensors are placed in specifically selected placements that avoid their respective pick up beams crossing each other, and
wherein said two or more sensors measure the same parameters, and the parameters are used by the device to minimize delivery of false alarms by the alarm generator.

2. The device according to claim 1, wherein the two or more sensors are placed each on a finger.

3. The device according to claim 2, wherein the placement of each of the sensors is on the base portion of each finger.

4. The device according to claim 1, wherein at least one of the two or more sensors is placed each on a zone of the palm of the hand.

5. The device according to claim 1, wherein the placement of each of the sensors is on the inner side of a wrist band or wrist watch.

6. The device according to claim 4, wherein the placement of the at least one sensor placed on a zones of the palm of the hand is at a portion near the base of the hand and distal from the thumb.

7. The device according to claim 1, wherein if none of the sensors is receiving a signal the device does not trigger an alarm.

8. The device according to claim 1, wherein if none of the sensors is receiving a signal a processor triggers a timer with a predetermined time delay.

9. The device according to claim 1, wherein if the sensors are all receiving signals below a certain predetermined alarm triggering threshold value the alarm generator will trigger the alarm output signal with zero delay.

10. The device according to claim 1, wherein if at least one sensor measures a value below a predefined alarm threshold and another sensor receives no signal, the output alarm signal is triggered without delay.

11. The device according to claim 1, wherein if at least one sensor measures a value below a predefined alarm threshold and another sensor receives no signal, the output alarm signal is triggered after a predefined delay.

12. The device according to claim 1, wherein one of the two or more pulse oximeter sensors measures blood oxygen saturation and another one of the two or more pulse oximeter sensors measures heart rate.

13. The device according to claim 1, wherein one of the two or more pulse oximeter sensors measures Heart Rate Variability (HRV).

14. The device according to claim 1, wherein at least two of the pulse oximeter sensors measure identical parameters.

15. The device according to claim 1, wherein each of said parameters has associated an independent timer.

16. The device according to claim 14, wherein as soon as the alarm is triggered by one of said parameters, the timer of another of the parameters is deactivated.

17. The device according to claim 1, wherein triggering of the alarm is blocked if one of the two or more sensors is measuring normal values, and the rest of the two or more sensors are measuring abnormal values.

18. The device according to claim 1, including a GPS function for controlling the user's geographical position and measuring the speed at which the user is moving, as soon as the device detects constant vehicle speed greater than a predetermined value during a predetermined period a personalized and autonomous alarm threshold setting program is activated for the user, and wherein the device triggers an alarm if the user's heart rate is below a predetermined threshold.

19. The device according to claim 1, wherein said device outputs measurement results and said measurement results are shown on a display mounted on the device, on a Smartphone or on a computer.

20. The device according to claim 1, wherein said device outputs measurement results and said measurement results are transmitted to said smartphone or said computer via a wired USB connection.

21. The device according to claim 1, wherein said device outputs measurement results and said measurement results are transmitted to said smartphone or said computer via a wireless connection.

22. The device according to claim 1, wherein, when the device is carried by the user and in contact with skin of the user, the device generates an alarm signal together with a transcutaneous electrical nervous stimulation on the skin of the user.

\* \* \* \* \*